United States Patent [19]

Schreibman

[11] Patent Number: 5,269,959
[45] Date of Patent: Dec. 14, 1993

[54] LIQUID DEEP CLEANING DETERGENT COMPOSITION

[76] Inventor: Gary Schreibman, P.O. Box 2746, La Mesa, Calif. 91943

[21] Appl. No.: 945,624

[22] Filed: Sep. 16, 1992

[51] Int. Cl.$^5$ .................. A61K 7/48; C11D 3/38; C11D 3/386; D06M 16/00

[52] U.S. Cl. .................. 252/100; 8/137; 252/89.1; 252/104; 252/106; 252/132; 252/143; 252/173; 252/174.12; 252/174.21; 252/DIG. 1; 252/DIG. 5; 252/DIG. 12; 252/DIG. 14; 424/76.1; 424/93 J; 435/263; 435/264; 435/854; 514/846; 514/947

[58] Field of Search ............... 252/89.1, 100, 104, 252/132, 173, 174.12, 174.21, DIG. 1, DIG. 5, DIG. 12, DIG. 14, 106; 424/93 J, 76.1; 435/263, 264, 854; 514/846, 947

[56] References Cited

U.S. PATENT DOCUMENTS

| | | | |
|---|---|---|---|
| 3,630,929 | 12/1971 | van Dijk | 252/136 |
| 4,316,812 | 2/1982 | Hancock | 252/99 |
| 4,345,032 | 8/1982 | Hata | 435/253 |
| 4,518,696 | 5/1985 | Gehrman | 435/253 |
| 4,525,351 | 6/1985 | Gehrman | 424/95 |
| 4,591,499 | 5/1986 | Linn | 424/93 J |
| 4,655,794 | 4/1987 | Richardson | 252/89.1 |
| 4,755,327 | 7/1988 | Bernaducci | 252/547 |
| 4,873,012 | 10/1989 | Broze | 252/99 |
| 5,085,999 | 2/1992 | Bowers-Irons | 435/264 |
| 5,176,911 | 1/1993 | Tosi | 424/93 J |

FOREIGN PATENT DOCUMENTS

| | | | |
|---|---|---|---|
| 0180743A | 5/1986 | European Pat. Off. | 424/93 H |
| 59-20220 | 2/1984 | Japan | 424/93 J |
| 2037160A | 7/1980 | United Kingdom . | |

*Primary Examiner*—Dennis Albrecht

[57] ABSTRACT

A deep-cleaning, topical surfactant in liquid form containing; polyethylene glycol alkylphenol ether containing 9 glycol units, Trypsin; Chymotrypsin; Pepsin; Lactobacillus Acidophilus; Ethanol; Hydrogen Peroxide, Acetic acid; and Deionized water.

6 Claims, No Drawings

LIQUID DEEP CLEANING DETERGENT COMPOSITION

BACKGROUND OF THE INVENTION

The present invention is directed toward a new and improved mixture of chemical elements which takes the form of a deep cleaning, topical surfactant in liquid form and which can be applied topically in liquid form on clothing and external body surfaces, functioning as a non-corrosive and non-staining cleaner. This mixture is also a disinfectant and odor eliminator. If less vigorous cleansing action is desired, the mixture can be diluted with distilled water.

SUMMARY OF THE INVENTION

In accordance with the principles of this invention, the mixture comprises the following nine elements:
polyethylene glycol alkylphenol ether containing 9 glycol units;
Trypsin;
Chymotrypsin;
Pepsin;
Lactobacillus Acidophilus;
Ethanol;
Hydrogen Peroxide;
Acetic acid; and
Deionized water.

In order to produce the mixture, solutions of the following elements are first mixed together to form a liquid host:
polyethylene glycol alkylphenol ether containing 9 glycol units;
Ethanol;
Hydrogen Peroxide;
Acetic acid;
Deionized water.

The following elements are blended together to form a dry blend:
Trypsin;
Chymotrypsin;
Pepsin;
Lactobacillus Acidophilus.

The dry blend is then carefully added to the liquid host to produce the final mixture.

The various elements should be present in the following relative proportions within specific ranges as defined in grams and as set forth below.

| ELEMENT | PARTS BY WEIGHT |
| --- | --- |
| polyethylene glycol alkylphenol ether containing 9 glycol units; | 0.05–12.5 |
| Trypsin; | 0.25–1.25 |
| Chymotrypsin; | 0.25–1.25 |
| Pepsin; | 0.25–1.25 |
| Lactobacillus Acidophilus; | 0.25–1.25 |
| Ethanol; | 0.25–1.25 |
| Hydrogen Peroxide; | 0.03–1.30 |
| Acetic acid; | 0.03–1.30 |
| Deionized water. | 0.25–1.25 |

DETAILED EXAMPLE

A specific composition of this surfactant is as follows.

| ELEMENT | PARTS IN WEIGHT |
| --- | --- |
| polyethylene glycol alkylphenol ether containing 9 glycol units; | 5 |
| Trypsin; | 0.75 |
| Chymotrypsin; | 0.75 |
| Pepsin; | 0.75 |
| Lactobacillus Acidophilus; | 0.75 |
| Ethanol; | 0.75 |
| Hydrogen Peroxide; | 0.30 |
| Acetic acid; | 0.30 |
| Deionized water. | 0.75 |

In order to produce the mixture, solutions of the following elements are first mixed together to form a liquid host:
polyethylene glycol alkylphenol ether containing 9 glycol units;
Ethanol;
Hydrogen Peroxide;
Acetic acid;
Deionized water.

These liquids are combined manually in a stainless steel vessel equipped with a hydro-mixing device in the following sequence; Deionized Water; polyethylene glycol alkylphenol ether containing 9 glycol units; Ethanol; Hydrogen Peroxide; and Acetic Acid. The hydro-mixing technique uses an electrical water pump which forces the liquid to flow gently in a circular motion in the cylindrical tank until all liquids are thoroughly blended at room temperature. Typically the circulation period is twenty minutes.

The following elements are blended together to form a dry blend:
Trypsin;
Chymotrypsin;
Pepsin;
Lactobacillus Acidophilus.

These elements are first blended together in their dry state in a horizontal stainless steel drum tumbler apparatus containing a number of stainless steel balls, each about one inch in diameter. The blending action is carried out at room temperature for a period of about twenty minutes at a rotational speed of thirty RPM.

While the liquid host is circulating in the hydro-mixer, the solid granules removed from the tumbler apparatus are slowly added through a sifted to assure a smooth liquid, avoiding lump formation.

The resultant product, a deep cleaning, topical surfactant in liquid form can be applied in undiluted form or can be diluted by adding distilled water thereto.

While the invention has been described in detail as set forth above, the protection sought is to be limited only by the terms of the claims which follow.

What is claimed is:

1. A deep cleaning topical surfactant liquid comprising:

| ELEMENT | PARTS BY WEIGHT |
| --- | --- |
| ; -polyethylene glycol alkylphenol ether containing 9 glycol units-. | 0.05–12.5 |
| Trypsin; | 0.25–1.25 |
| Chymotrypsin; | 0.25–1.25 |
| Pepsin; | 0.25–1.25 |
| Lactobacillus Acidophilus; | 0.25–1.25 |
| Ethanol; | 0.25–1.25 |
| Hydrogen Peroxide; | 0.03–1.30 |
| Acetic acid; | 0.03–1.30 |

| ELEMENT | PARTS BY WEIGHT |
|---|---|
| -continued | |
| Deionized water. | 0.25–1.25 |

2. The liquid of claim 1 wherein the proportions of the liquid are as follows:

| ELEMENT | PARTS BY WEIGHT |
|---|---|
| polyethylene glycol alkylphenol ether containing 9 glycol units; | 5 |
| Trypsin; | 0.75 |
| Chymotrypsin; | 0.75 |
| Pepsin; | 0.75 |
| Lactobacillus Acidophilus; | 0.75 |
| Ethanol; | 0.75 |
| Hydrogen Peroxide; | 0.30 |
| Acetic acid; | 0.30 |
| Deionized water. | 0.75 |

3. A method for producing the surfactant liquid of claim 1 comprising the following steps:
   mixing together solutions of the following elements to form a liquid host:
   polyethylene glycol alkylphenol ether containing 9 glycol units;
   Ethanol;
   Hydrogen Peroxide;
   Acetic acid;
   Deionized water;
   blending together in dry form the following elements to form a dry blend:
   Trypsin;
   Chymotrypsin;
   Pepsin;
   Lactobacillus Acidophilus; and
   adding the dry blend to the liquid host to produce the final mixture.

4. The method of claim 3 wherein step is performed by combining the liquids manually in a stainless steel vessel equipped with a hydro-mixing device.

5. The method of claim 4 wherein step is performed by blending the solids in dry state in a stainless steel drum tumbler apparatus.

6. The method of claim 5 wherein step is performed by circulating the liquid of step a in said vessel while adding the dry blend to the liquid through a sifter.

* * * * *